(12) United States Patent
Perkins et al.

(10) Patent No.: US 7,838,303 B2
(45) Date of Patent: Nov. 23, 2010

(54) PEPTIDE DERIVATIZATION METHOD TO INCREASE FRAGMENTATION INFORMATION FROM MS/MS SPECTRA

(75) Inventors: Patrick D. Perkins, Sunnyvale, CA (US); Steven M. Fischer, Hayward, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 990 days.

(21) Appl. No.: 11/494,383

(22) Filed: Jul. 27, 2006

(65) Prior Publication Data

US 2008/0026479 A1    Jan. 31, 2008

(51) Int. Cl.
*G01N 24/00* (2006.01)
(52) U.S. Cl. .............................. 436/173; 436/86; 436/89
(58) Field of Classification Search .................. None
See application file for complete search history.

(56) References Cited

U.S. PATENT DOCUMENTS

| | | |
|---|---|---|
| 2003/0119069 A1 | 6/2003 | Schneider |
| 2003/0153007 A1 | 8/2003 | Chen et al. |
| 2004/0161795 A1 | 8/2004 | Marto |
| 2004/0209251 A1 | 10/2004 | Schneider |

OTHER PUBLICATIONS

Carter "Vonjugate of Peptodes to Carrier Protein via Carbodiimide" from "The Protein Protocols Handbook", 1996, p. 693.*
GB Search Report, Nov. 6, 2007.
T. Nakazawa et al., "Enhanced responses in matrix-assisted laser desorption/ionization mass spectrometry of peptides derivatized with arginine via a C-terminal oxazolone", Rapid Communications in Mass Spectrometry, vol. 18, pp. 799-807 (2004).

* cited by examiner

*Primary Examiner*—Yelena G Gakh

(57) ABSTRACT

A method of facilitating analysis of a peptide in a mass spectrometer comprising derivatizing the C-terminus of the peptide with an amino acid residue via a reaction with a carbodiimide reagent, yielding a derivative peptide, ionizing the derivative peptide with a double charge, and fragmenting the ionized derivative peptide in a mass spectrometry system, wherein binary fragments of the ionized derivative each include a charge, facilitating sequence analysis of the peptide.

10 Claims, 4 Drawing Sheets

--Prior Art--

--Prior Art--

Ala-Ala-Ala

--Prior Art--

US 7,838,303 B2

PEPTIDE DERIVATIZATION METHOD TO INCREASE FRAGMENTATION INFORMATION FROM MS/MS SPECTRA

BACKGROUND INFORMATION

Proteins are typically identified through a series of distinct procedures. The protein(s) of interest are first separated and isolated, and then digested with an enzyme to create a mixture of peptides. The peptides are then analyzed using tandem mass spectrometry (MS/MS) to obtain a fragmentation pattern characteristic of the peptides. An identification procedure follows which generally employs database searching techniques to compare the fragmentation pattern data with other known patterns.

The enzyme most prevalently used in the digestion procedure is trypsin, which cleaves the protein on the C-terminal side of lysine or arginine residues. Trypsin is favored because lysine and arginine are present at about 11.7% of all peptide residues; consequently, peptides which emerge from digestion by trypsin typically contain between 6 and 25 amino acid residues, with an average of about ten amino acid residues. Peptides of this relatively short length have a molecular weight within a range that can be accommodated by most mass spectrometers. An additional benefit of trypsin digestion is that the presence of the basic lysine or arginine at the C-terminus in conjunction with the basic N-terminus yields doubly charged ions under the ionization conditions of ESI MS/MS analysis. A routine method to determine the amino acid sequence of these doubly-charged ions is to fragment them by "collision-induced dissociation" (CID) in a mass spectrometer. CID it typically performed by accelerating the peptide ions in a controlled fashion and forcing them to collide with inert gas molecules such as nitrogen or argon. As a result of one or more such collisions, these doubly-charged peptide ions have been found to fragment in a predictable way that yields useful information about the peptide in question. In particular, the presence of 'b-ions' and 'y-ions' in the CID fragment spectra is diagnostic enough to enable automated database searching algorithms to assign a peptide sequence with a high degree of confidence. It should be noted that other diagnostically useful peptide ions are produced as well by the CID process, such as a-, c-, x-, and z-ions. FIG. 4 illustrates various fragmentation ions of an example peptide including three alanine molecules. As shown, the peptide can fragment in different places along the peptide backbone. The $a_m$-$x_{n-m}$ fragments are created by a break between a carbon and the carboxyl bond, the $b_m$-$y_{n-m}$ fragments are created by a break on the N-terminal side of amide bonds, while $c_m$-$z_{n-m}$ fragments are created by a break on the C-terminal side of amide bonds in the backbone.

There are, however, classes of proteins that do not contain the average numbers of lysine or arginine residues. For example, membrane proteins include long spans of hydrophobic amino acid residues without lysine or arginine. When proteins that do not contain the average numbers of lysine or arginine residues are digested with trypsin, large sections of the insoluble protein having masses above the range of most mass spectrometers remain intact and thus cannot be identified by MS/MS.

While it is possible to use other enzymes or chemical digestion techniques for the proteins unamenable to trypsin digestion, peptides produced by cleavage by other enzymes or reagents generally do not have a basic lysine or arginine residue at the C-terminus and thus tend to produce singly-charged rather than doubly-charged precursor ions. Such singly-charged precursor ions do not produce the rich series of b-ions and y-ions and therefore tend to yield less useful sequence information when fragmented in a mass spectrometer.

It would therefore be of great use to provide a method of analyzing proteins normally indigestible using trypsin that can still yield the useful sequence information obtainable from trypsin-produced peptides.

SUMMARY OF THE INVENTION

To address this problem, the present invention provides a method for derivatizing a peptide to include an arginine or lysine residue, so that its behavior corresponds to a 'tryptic peptide' during ionization and fragmentation.

In particular, the present invention provides a method of facilitating analysis of a peptide in a mass spectrometer that comprises derivatizing the C-terminus of the peptide with an amino acid residue via a reaction with a carbodiimide reagent, yielding a derivative peptide, ionizing the derivative peptide with a double charge, and fragmenting the ionized derivative peptide in a mass spectrometry system. The binary fragments of the ionized derivative each include a charge, which facilitating sequence analysis of the peptide. The amino acid residue may be either arginine or lysine, which are basic and tend to accept a proton during ESI LC/MS/MS conditions.

DETAILED DESCRIPTION

As used in this specification and the appended claims, the singular forms "a," "an," and "the" include plural referents unless the context clearly dictates otherwise.

According to the present invention, a peptide to be analyzed, that is not digestible using trypsin, is modified by coupling an arginine or lysine derivative to the C-terminus of the peptide. During ionization, the peptide modified in this manner becomes doubly-charged since the C-terminus of the modified peptide includes a basic arginine or lysine residue which tends to pick up a protein during ionization. This modification provides favorable fragmentation behavior, enabling the recovery of strong b- and y-ion abundances that appear in fragment spectra. From this informative data, the amino acid sequence of the peptide can be identified.

Figure 1:
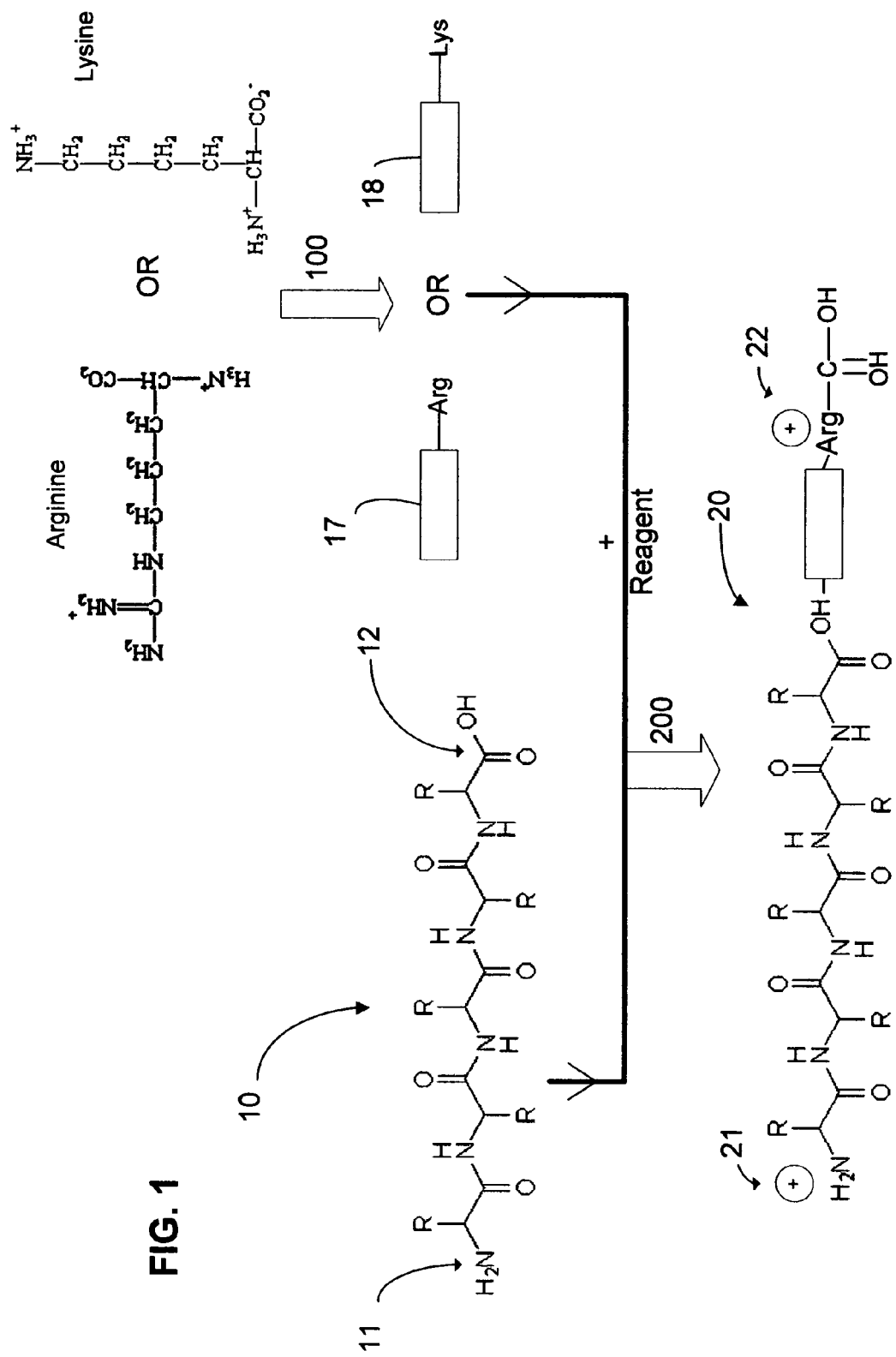
FIG. 1 shows a schematic illustration of an embodiment of the peptide derivatization method of the present invention

FIG. 1 is a schematic illustration of an embodiment of the method of the present invention. A peptide 10 having an N-terminus 11, a C-terminus 12 and a number of linked amino acid residues is presented for analysis. For the purposes set forth, the peptide 10 may include no or few arginine or lysine residues, rendering digestion of the peptide with trypsin unfeasible. If the length of peptide 10 is too large to be accommodated by most mass spectrometers, it can be broken into smaller peptides by digestion using other enzymes and/or chemical reagents.

In a first process 100 arginine and/or lysine are derivatized using techniques well known in the art to yield arginine and/or lysine derivatives 17, 18 which include an arginine or lysine residue coupled via the N-terminal to an organic molecule, such as an ester, or additional amino residues. In a second process, the arginine 17 and/or lysine 18 derivative is coupled to the C-terminus 12 of peptide 10 in the presence of one or more reagents 25 using a peptide synthesis technique 200. According to one exemplary embodiment, the peptide synthesis is performed using carbodiimide reagents described with reference to FIG. 2 below. It is noted that other peptide synthesis techniques may also be employed to couple the peptide 10 with the arginine and/or lysine derivative 17, 18. The result of the synthesis 200 is a modified peptide 20 that includes an arginine or lysine residue at its C-terminus 22. In solution or during ionization, both the N-terminus 21 and the arginine/lysine residue at the C-terminus 21 of the modified peptide 20 tend to pick up a proton (+), so that the original peptide 10 which would tend to become singly-charged without modification, is converted to enable double-charging.

As noted, during MS/MS the modified peptide is fragmented. Since the charges on the modified peptide are located at either of the N and C-terminals, the fragments are composed of ion pairs constituting one ion on the left side of a cleavage and another on the right side of the cleavage. Ions that retain their charge on the N-terminus after fragmentation between the "XXXX" bond of the precursor are denoted as y-ions, and those that retain their charge on the C-terminus after fragmentation between the "XXXX" bond of the precursor are denote as b-ions. The difference in m/z values between consecutive ions within a given series corresponds to the difference in the sequences of the two fragments. Because the consecutive ions within a series represent peptide fragments that differ in exactly one amino acid, and each amino acid residue has a unique normal weight (expect for leucine and isoleucine), the pattern of m/z values of y- and b-ions corresponds to the amino acid sequence of the precursor peptide.

It is noted that while CID is the most commonly used fragmentation mechanism in MS/MS, other fragmentation techniques can be employed in the context of the present invention to fragment the derivatized peptide ions such as electron capture dissociation (ECD) and electron transfer dissociation (ETD). In ECD, positively charged peptides capture low-energy electrons emitted from an electron source. The capture of the electron brings about the formation of radical species that causes the peptide to cleave. It has been found that this technique is particularly applicable to studying post-translational modifications that are often not preserved during the more robust CID process. In ETD, singly-charged anions with low electron affinity transfer an electron to positively charged peptides by ion/ion interaction. This technique is also particularly useful in the study of post-translational modifications, and has the advantage that it may be easier to apply this technique in standard mass analyzers because anions are more easily trapped by RF fields than electrons.

Figure 2A:
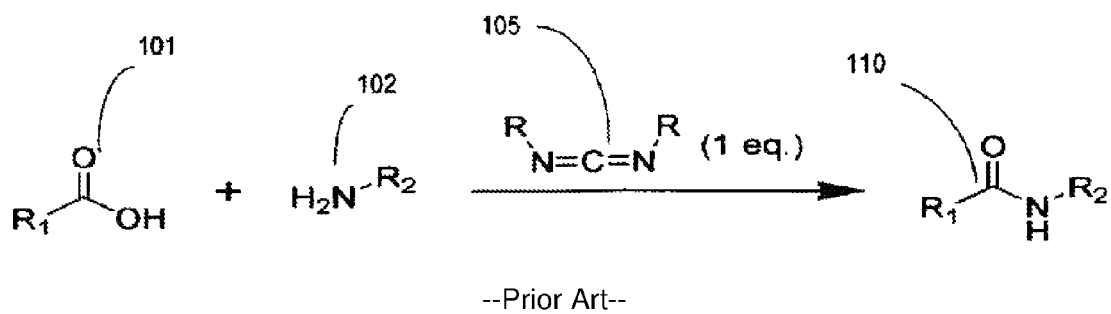
FIG. 2A shows an exemplary chemical formula for peptide synthesis via a carbodiimide reagent.

FIG. 2A illustrates, in general form, an exemplary chemical formula through which the process of coupling an arginine or lysine residue to a peptide may be implemented, which makes use of a carbodiimide reagent. In this process an amide bond is created between the C-terminal a first peptide 101 having a residue $R_1$ (which may include one or more amino acids) and the N-terminal of a second peptide 102 having a residue $R_2$, which may be arginine or lysine, creating a modified peptide 110 including both $R_1$ and $R_2$. This process occurs through the intermediary participation of a carbodiimide molecule 105. Carbodiimides that may be used in this context include N,N'-dicyclehexyl-carbodiimide (DCC) and 1-ethyl-3-(3-dimethylaminopropyl)carbodiimide hydrochloride (EDC).

Figure 2B:
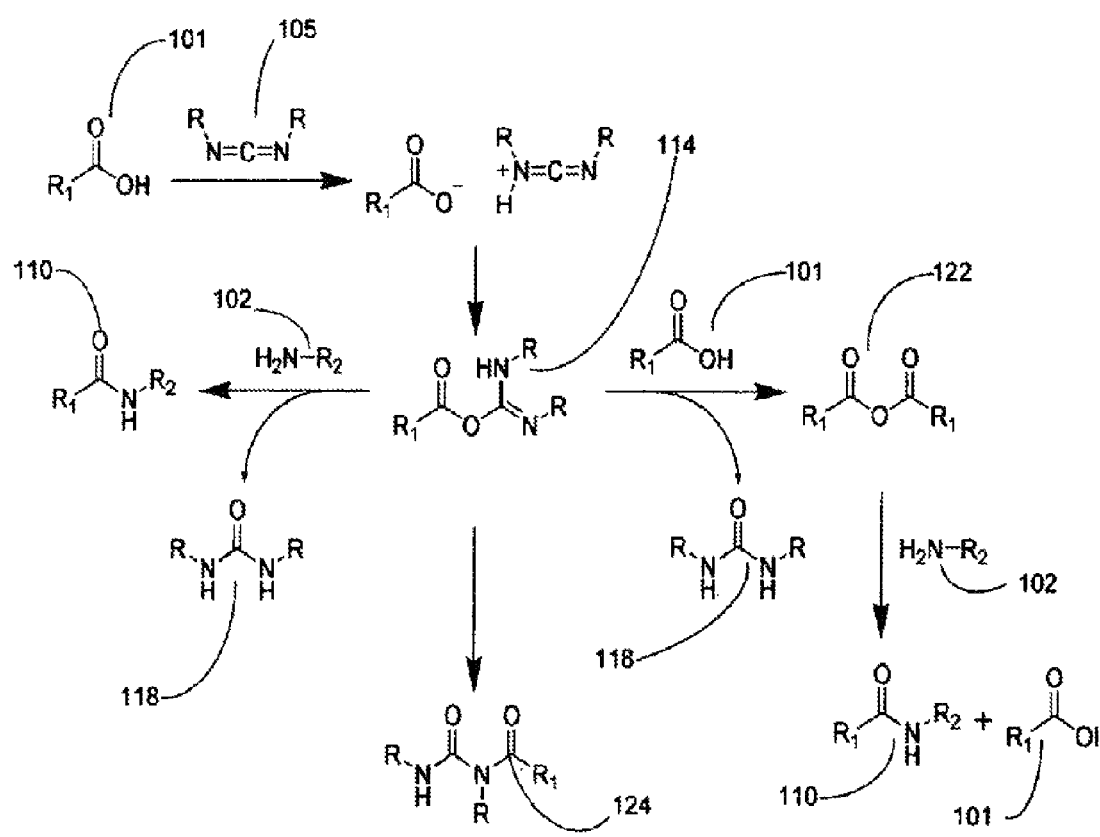
FIG. 2B illustrates potential chemical pathways of the peptide synthesis process via a carbodiimide reagent summarized in the formula of FIG. 2A.

FIG. 2B illustrates an exemplary carbodiimide amide formation mechanism in greater detail. In a first step, the carbodiimide 105 reacts with the C-terminal of the first peptide 101 in an acid base reaction, whereby the peptide donates a proton to the carbodiimide. After the proton exchange, the first peptide and the carbodiimide combine to form an intermediate product, O-acylisourea 114, which is a carboxylic ester. The O-acylisourea 114 will react with the N-terminal of the second peptide 102 to produce the modified peptide 110 sought and urea 118. In side reactions, O-acylisourea 114 can react with the C-terminal of remaining first peptide 101 to produce a carboxylic anhydride 122, which can react further with the N-terminal of the second peptide 102 to yield the desired modified peptide 110. However, the intermediate O-acylisourea 114 can also stabilize through rearrangement into N-acylurea 124. Since this pathway does not lead to the formation of the modified peptide 110, it is preferable to take steps to prevent this side reaction from occurring. It has been found that using a solvent with a low dielectric constant such as dichloromethane or chloroform minimizes this undesired side reaction.

While peptide synthesis through carbodiimide chemistry is thought to be particularly suitable for the peptide derivatization method disclosed herein, it is emphasized that other peptide synthesis methods may also be used in the context of the present invention.

EXAMPLE

Figure 3A:
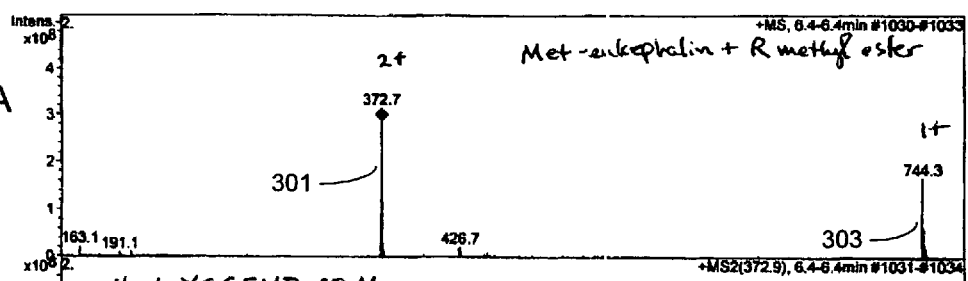
FIG. 3A is a mass spectrum of a methionine-enkephalin molecule derivatized with arginine methyl ester.
Figure 3B:
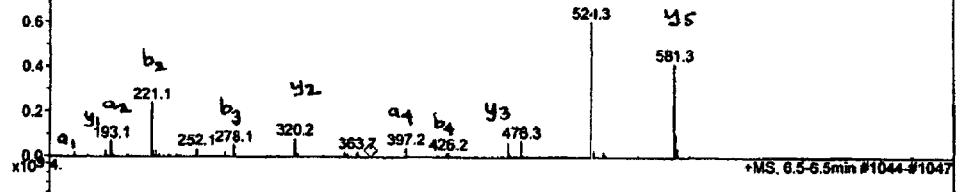
FIG. 3B is a fragment spectrum of the doubly-charged ion of methionine-enkephalin molecule derivatized with arginine methyl ester.
Figure 3C:
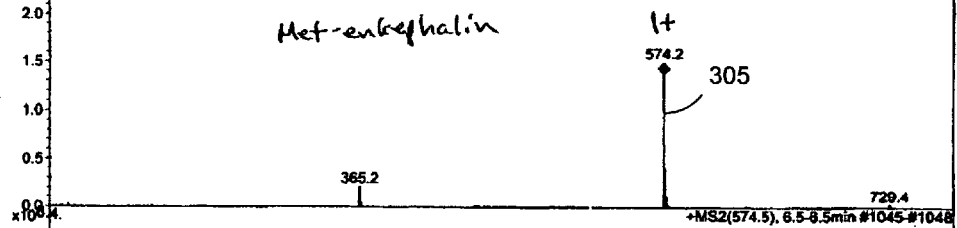
FIG. 3C is a mass spectrum of un-derivatized methionine-enkephalin.
Figure 3D:
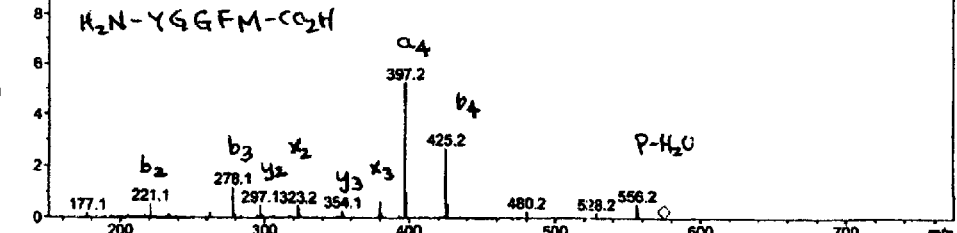
FIG. 3D is a fragmentation of a single-charged precursor ion of methionione-enkaphalin.
Figure 4:
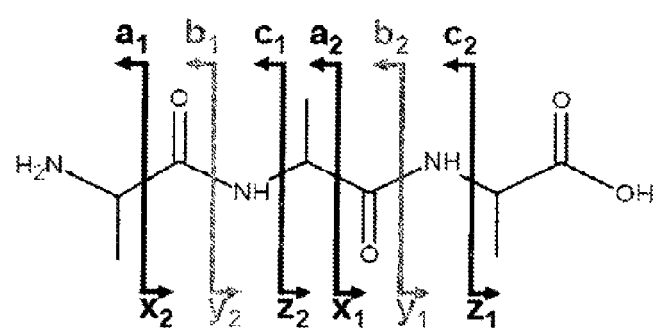
FIG. 4 showing the various fragmentation ions of an example peptide including three alanine molecules.

A pentapeptide, methionine-enkephalin was used as an exemplary hydrophobic peptide containing no basic or acidic groups except at its C and N terminals. Arginine was derivatized and through addition of a carbodiimide reagent, an arginine methyl ester was formed. The arginine methyl ester was then coupled to the methionine-enkephalin to produce a peptide with six residues (hexapeptide) bearing arginine methyl ester at the C-terminus. FIG. 3A illustrates a mass spectrum of the hexapeptide prior to fragmentation. This mass spectrum shows both doubly charged 301 and singly charge 303 ions. FIG. 3B illustrates a fragment spectrum of the doubly-charged precursor having a complete y-ion series and most of the b-ions (eight out of ten total). This may be contrasted with spectra of the original methionine-enkephalin peptide that was not derivatized with an arginine or lysine residue. FIG. 3C shows that the methionine-enkephaline produces only a singly-charged ion 305 while in the corresponding fragment spectrum, shown in FIG. 3D, few b- and y-ions appear (four of ten), and all are of low abundance.

Having described the present invention with regard to specific embodiments, it is to be understood that the description is not meant to be limiting since further modifications and variations may be apparent or may suggest themselves to those skilled in the art. It is intended that the present invention cover all such modifications and variations as fall within the scope of the appended claims.

What is claimed is:

1. A method of facilitating analysis of a peptide having an N-terminus and a C-terminus in a mass spectrometer comprising:

derivatizing the C-terminus of the peptide with an amino acid residue via a reaction with a carbodiimide reagent, yielding a derivative peptide;

ionizing the derivative peptide to produce a doubly charged derivative peptide; and fragmenting said doubly charged derivative peptide in a mass spectrometry system to produce a N-terminal fragment and a C-terminal fragment of said doubly charged derivative peptide;

wherein said N-terminal fragment and said C-terminal fragment each include a charge, facilitating sequence analysis of the peptide.

2. The method of claim 1, wherein the amino acid residue includes at least one of lysine and arginine.

3. The method of claim 1, wherein the N and C termini of the derivative peptide are charged by the ionizing.

4. The method of claim 3, wherein the fragmenting of the derivative peptide produces a substantial majority of a y-ion series and a b-ion series.

5. The method of claim 1, wherein the peptide prior to derivatization is hydrophobic.

6. The method of claim 5, wherein the peptide does not include lysine or arginine residues prior to derivatization.

7. The method of claim 6, wherein the peptide comprises a membrane protein.

8. The method of claim 1, wherein the fragmenting step is performed by collision-induced dissociation (CID).

9. The method of claim 1, wherein the fragmenting step is performed by electron-capture dissociation (ECD).

10. The method of claim 1, wherein the fragmenting step is performed by electron-transfer dissociation (ETD).

* * * * *

UNITED STATES PATENT AND TRADEMARK OFFICE
CERTIFICATE OF CORRECTION

PATENT NO. : 7,838,303 B2
APPLICATION NO. : 11/494383
DATED : November 23, 2010
INVENTOR(S) : Patrick D. Perkins et al.

It is certified that error appears in the above-identified patent and that said Letters Patent is hereby corrected as shown below:

On the Title page, in field (56), under "Other Publications", in column 2, line 1, delete "Vonjugate of Peptodes" and insert -- Conjugation of Peptides --, therefor.

Signed and Sealed this
First Day of February, 2011

David J. Kappos
*Director of the United States Patent and Trademark Office*